(12) United States Patent
Suhir et al.

(10) Patent No.: US 8,048,688 B2
(45) Date of Patent: Nov. 1, 2011

(54) METHOD AND APPARATUS FOR EVALUATION AND IMPROVEMENT OF MECHANICAL AND THERMAL PROPERTIES OF CNT/CNF ARRAYS

(75) Inventors: Ephraim Suhir, Los Altos, CA (US); Yuan Xu, Milpitas, CA (US); Yi Zhang, Sunnyvale, CA (US)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1111 days.

(21) Appl. No.: 11/618,441

(22) Filed: Dec. 29, 2006

(65) Prior Publication Data

US 2008/0096293 A1 Apr. 24, 2008

Related U.S. Application Data

(60) Provisional application No. 60/862,664, filed on Oct. 24, 2006.

(51) Int. Cl.
*H01L 21/66* (2006.01)
(52) U.S. Cl. ........................................................ 438/14
(58) Field of Classification Search .................. None
See application file for complete search history.

(56) References Cited

U.S. PATENT DOCUMENTS

| | | | |
|---|---|---|---|
| 4,466,618 A | 8/1984 | Angelini | |
| 4,932,052 A | 6/1990 | Lo | |
| 5,060,543 A | 10/1991 | Warheit | |
| 5,195,378 A | 3/1993 | Ferguson | |
| 5,217,094 A | 6/1993 | Walter et al. | |
| 5,713,690 A | 2/1998 | Corbin, Jr. et al. | |
| 5,808,236 A | 9/1998 | Brezina et al. | |
| 5,818,700 A | 10/1998 | Purinton | |

(Continued)

FOREIGN PATENT DOCUMENTS

EP 1329953 8/2003

(Continued)

OTHER PUBLICATIONS

Banerjee, K. et al. "3-D Heterogeneous ICs: a Technology for the Next Decade and Beyond." $5^{th}$ IEEE Workshop on Signal propagation on Interconnects, Venice, Italy, May 13-15, 2001.

(Continued)

*Primary Examiner* — Charles Garber
*Assistant Examiner* — Andre' C Stevenson
(74) *Attorney, Agent, or Firm* — Harness, Dickey & Pierce, P.L.C.

(57) ABSTRACT

A method and apparatus for the evaluation and improvement of the mechanical and thermal properties of carbon-nanotube (CNT) and carbon nanofiber (CNF) arrays grown on a substrate is disclosed. The Young's modulus of a CNT/CNF material is measured by applying an axial compressive force on the CNT/CNF array and measuring the applied forces and the induced displacements. Also disclosed are the evaluation of the nonlinear stress-strain relationship of the CNT/CNF material, increasing of the Young's modulus and decreasing the thermal resistance by application of a compressive load, the application of rapid thermal annealing to improve the quality of the CNT/CNF material and to reduce the interfacial thermal resistance, improvement of the bonding strength of the CNT/CNF array to a substrate, evaluation of the bonding strength of the CNT/CNF array to a substrate, evaluation of the shearing force at failure, and an analytical stress model that enables one to predict the interfacial shearing stress from the measured force.

18 Claims, 7 Drawing Sheets

U.S. PATENT DOCUMENTS

| | | | |
|---|---|---|---|
| 5,837,081 | A | 11/1998 | Ting |
| 5,932,925 | A | 8/1999 | McIntyre |
| 5,965,267 | A | 10/1999 | Nolan |
| 5,990,552 | A | 11/1999 | Xie et al. |
| 6,156,256 | A | 12/2000 | Kennel |
| 6,180,874 | B1 | 1/2001 | Brezina et al. |
| 6,231,744 | B1 | 5/2001 | Ying |
| 6,232,706 | B1 | 5/2001 | Dai |
| 6,340,822 | B1 | 1/2002 | Brown |
| 6,359,288 | B1 | 3/2002 | Ying |
| 6,361,861 | B2 | 3/2002 | Gao |
| 6,373,703 | B2 | 4/2002 | Johnson et al. |
| 6,383,923 | B1 | 5/2002 | Brown |
| 6,395,991 | B1 | 5/2002 | Dockerty et al. |
| 6,407,922 | B1 | 6/2002 | Eckblad |
| 6,417,563 | B1 | 7/2002 | Halderman et al. |
| 6,432,740 | B1 | 8/2002 | Chen |
| 6,449,155 | B1 | 9/2002 | Colbert et al. |
| 6,504,292 | B1 | 1/2003 | Choi |
| 6,591,658 | B1 | 7/2003 | Yedur |
| 6,599,961 | B1 | 7/2003 | Pienkowski et al. |
| 6,618,251 | B2 | 9/2003 | Ishimine |
| 6,713,151 | B1 | 3/2004 | Dean |
| 6,724,906 | B2 | 4/2004 | Naksen et al. |
| 6,756,026 | B2 | 6/2004 | Colbert |
| 6,800,886 | B2 | 10/2004 | Awano |
| 6,821,415 | B2 | 11/2004 | Sharb |
| 6,853,068 | B1 | 2/2005 | Djekic |
| 6,855,376 | B2 | 2/2005 | Hwang |
| 6,856,016 | B2 | 2/2005 | Searls |
| 6,856,511 | B1 | 2/2005 | Viernes et al. |
| 6,859,367 | B2 | 2/2005 | Davison |
| 6,862,962 | B1 | 3/2005 | Delbrugge, Jr. et al. |
| 6,864,571 | B2 | 3/2005 | Arik |
| 6,880,799 | B2 | 4/2005 | Mrozek |
| 6,891,724 | B2 | 5/2005 | De Lorenzo |
| 6,892,652 | B2 | 5/2005 | Jalbert et al. |
| 6,900,580 | B2 | 5/2005 | Dai |
| 6,910,666 | B2 | 6/2005 | Burr |
| 6,921,462 | B2 | 7/2005 | Montgomery |
| 6,924,335 | B2 | 8/2005 | Fan |
| 6,955,800 | B2 | 10/2005 | Resasco et al. |
| 6,962,823 | B2 | 11/2005 | Empedocles |
| 6,965,513 | B2 | 11/2005 | Montgomery |
| 6,989,325 | B2 | 1/2006 | Uang |
| 6,998,358 | B2 | 2/2006 | French et al. |
| 7,008,604 | B2 | 3/2006 | Smalley |
| 7,011,771 | B2 | 3/2006 | Gao |
| 7,029,646 | B2 | 4/2006 | Margrave |
| 7,033,647 | B2 | 4/2006 | Tang et al. |
| 7,052,666 | B2 | 5/2006 | Colbert |
| 7,109,581 | B2 | 9/2006 | Dangelo et al. |
| 2002/0090501 | A1 | 7/2002 | Tobita |
| 2002/0100581 | A1 | 8/2002 | Knowles |
| 2002/0130407 | A1 | 9/2002 | Dahl |
| 2002/0145194 | A1 | 10/2002 | O'Conner |
| 2002/0159943 | A1 | 10/2002 | Smalley et al. |
| 2002/0163079 | A1 | 11/2002 | Awano |
| 2003/0111333 | A1 | 6/2003 | Montgomery |
| 2003/0117770 | A1 | 6/2003 | Montgomery |
| 2003/0231471 | A1 | 12/2003 | De Lorenzo |
| 2004/0005736 | A1 | 1/2004 | Searls |
| 2004/0013598 | A1 | 1/2004 | McElrath |
| 2004/0053053 | A1 | 3/2004 | Jiang |
| 2004/0101468 | A1 | 5/2004 | Liu |
| 2004/0136161 | A1 | 7/2004 | Miyamura et al. |
| 2004/0146560 | A1 | 7/2004 | Whiteford |
| 2004/0150100 | A1 | 8/2004 | Dubin |
| 2004/0152240 | A1 | 8/2004 | Dangelo |
| 2004/0182600 | A1 | 9/2004 | Kawabata |
| 2004/0184241 | A1 | 9/2004 | De Lorenzo |
| 2004/0191158 | A1 | 9/2004 | Liu |
| 2004/0218362 | A1 | 11/2004 | Amaro |
| 2004/0261978 | A1 | 12/2004 | Zhan |
| 2004/0261987 | A1 | 12/2004 | Zhang |
| 2004/0265489 | A1 | 12/2004 | Dubin |
| 2004/0266063 | A1 | 12/2004 | Montgomery |
| 2004/0266065 | A1 | 12/2004 | Zhang |
| 2005/0006754 | A1 | 1/2005 | Arik |
| 2005/0037204 | A1 | 2/2005 | Osiander |
| 2005/0046017 | A1 | 3/2005 | Dangelo |
| 2005/0061496 | A1 | 3/2005 | Matabayas |
| 2005/0067693 | A1 | 3/2005 | Nihei |
| 2005/0092464 | A1 | 5/2005 | Leu |
| 2005/0116336 | A1 | 6/2005 | Chopra |
| 2005/0136248 | A1 | 6/2005 | Leu |
| 2005/0139642 | A1 | 6/2005 | Koning |
| 2005/0139991 | A1 | 6/2005 | White |
| 2005/0150887 | A1 | 7/2005 | Taya |
| 2005/0167647 | A1 | 8/2005 | Huang |
| 2005/0224220 | A1 | 10/2005 | Li |
| 2005/0238810 | A1 | 10/2005 | Scaringe |
| 2005/0260412 | A1 | 11/2005 | Gardner |
| 2005/0269726 | A1 | 12/2005 | Matabayas, Jr. |
| 2006/0073712 | A1 | 4/2006 | Suhir |
| 2006/0166003 | A1 | 7/2006 | Khabashesku et al. |
| 2006/0279679 | A1* | 12/2006 | Fujisawa et al. .............. 349/116 |
| 2007/0091572 | A1* | 4/2007 | Schulz-Harder et al. ..... 361/704 |
| 2007/0126966 | A1* | 6/2007 | Takahashi ..................... 349/130 |
| 2008/0170982 | A1* | 7/2008 | Zhang et al. ............... 423/447.3 |

FOREIGN PATENT DOCUMENTS

| | | |
|---|---|---|
| WO | WO 03/054958 | 7/2003 |
| WO | WO 03/072679 | 9/2003 |
| WO | WO 03/107419 | 12/2003 |

OTHER PUBLICATIONS

Berber et al. "Unusually High Thermal Conductivity of Carbon Nanotubes, Physical Review Letters." May 15, 2000, pp. 4613-4616, vol. 84, No. 20.

Cassell, a. "Direct Growth of Free-standing single-Walled Carbon Nanotubes." J. Am. Chemical society, 1999, 121, pp. 7975-7976.

Chiang, T.Y. "A New Analytical Thermal Model for Multilevel ULSI Interconnects Incorporating Via Effect." Center for Integrated Systems, Stanford University.

Chiang, T.Y. "Effect of Via Separation and Low-k Dielectric Materials on the Thermal Characteristics of Cu Interconnects." IEDM 2000.

Cui, Y. et al. "Doping and Electrical Transport in Silicon Nanowires." Journal of Physical Chemistry, vol. 104, No. 22, Jun. 8, 2000, pp. 5213-5216.

de Pablo, P.J. "A Simple, Reliable Technique for Making Electrical Contact to Multiwalled Carbon Nanotubes." Applied Physics Letters, vol. 74, No. 2, Jan. 11, 1999, pp. 323-325.

Delzeit, L. et al. "Growth of Carbon Nanotubes by Thermal and Plasma Chemical Vapour Deposition Processes and Applications in Microscopy." Nanotechnology, vol. 13, May 23, 2002, pp. 280-284.

Delzeit, L. et al. "Growth of Multiwall Carbon Nanotubes in an Inductively Coupled Plasma Reactor." Journal of Applied Physics, vol. 91, No. 9, May 1, 2002, pp. 6027-6033.

Goodson, K.E. et al. "Improved Heat Sinking for Laser-Diode Arrays Using Microchannels in CBD Diamond." IEE Transactions on Components, Packaging, and Manufacturing Technology, Part B, Advanced Packaging, vol. 20, Issue 1, Feb. 1997, pp. 104-109.

Hone, J. et al. "Thermoelectric Power of Single-Walled Carbon Nanotubes." Physical Review Letters, vol. 80, No. 5, Feb. 2, 1998, pp. 1042-1045.

Huang, Z.P. et al. "Growth of Highly Oriented Carbon Nanotubes by Plasma-Enhanced Hot Filament Chemical Vapor Deposition." Applied Physics Letters, vol. 73, No. 26, Dec. 28, 1998, pp. 3845-3847.

International Semiconductor Road Map (ITRS-2001), Section on Interconnect, http://public/itrs.net/files/2001ITRS/interconnect.pdf.

Kim, M.J. et al. "Growth Characteristics of Carbon Nanotubes via Aluminum Nanopore Template on Si Substrate Using PECVD." Elsevier Thin Solid Films, vol. 425, 2003, pp. 312-317.

Kong, J. et al. "Synthesis of Individual Single-Walled Carbon Nanotubes on Patterned Silicon Wafers." Nature, vol. 395, Oct. 29, 1998, pp. 878-881.

Kurabayashi, K. et al. "Precision Measurement and Mapping of die-attach Termal Resistance." IEEE Transactions on Components, Packaging, and Manufacturing Technology, Part A: Advanced Packaging, vol. 21, Issue 3, Sep. 1998, pp. 506-514.

Li, J. et al. "Controlled Deposition of Individual Single-Walled Carbon Nanotubes on Chemically Functionalized Templates." Chemical Physics Letters, 303, Apr. 2, 1999, pp. 125-129.

McEuen, P.L. et al. "Single-walled Carbon Nanotube Electronics." IEEE Transactions on Nanotechnology, vol. 1, No. 1, Mar. 2002, pp. 78-85.

Meyyappan, M. et al. "Carbon Nanotube Growth by PECVD: a Review." Plasma Sources Science and Technology, vol. 12, Apr. 2, 2003, pp. 205-216.

Ren, Z.F., et al., "Synthesis of Large Arrays of Well-Aligned Carbon Nanotubes on Glass." Science, vol. 282, Nov. 6, 1998, pp. 1105-1107.

Shi, L. "A Microdevice for Measuring Thermophysical Properties of Nanowires and Nanotubes." 2001 ASME International Mechanical Engineering Congress and Exposition, Nov. 11-16, 2001, pp. 359-362.

Shi, L. "Scanning Thermal Microscopy of Carbon Nanotubes Using Batch-Fabricated Probes." Applied Physics Letters, vol. 77, No. 26, Dec. 25, 2000, pp. 4295-4297.

Stevens, R. "Improved Fabrication Approach for Carbon Nanotube Probe Devices." Applied Physics Letters, vol. 77, No. 21, Nov. 20, 2000, pp. 3453-3455.

Sun, X. et al. "Theoretical Modeling of Thermoelectricity in Bi Nanowires." Applied Physics Letters, vol. 74, No. 26, Jun. 28, 1999, pp. 4005-4007.

Tu et al. "Growth of Aligned Carbon Nanotubes with Controlled Site Density." Applied Phys. Letters, American Institute of Physics, May 27, 2002, pp. 4018-4020, vol. 80, No. 21.

Yakobson, B.I. et al. "Fullerene Nanotubes: C1,000,000 and Beyond." American Scientist online, http://www.americanscientist,org/template/AssetDetail/assetid/2870?fulltext=true&print=yes.

Zhang, "Formation of Metal Nanowires on Suspended Single-Walled Carbon Nanotubes." Appl. Phys. Lett., vol. 77(19), p. 3015 (2000.

Zhang, W.D. et al. "Synthesis of Vertically Aligned Carbon Nanotubes Films on Silicon Wafers by Pyrolysis of Ethylenediamine." Elsevier, Thin Solid Films, 422, 2002, pp. 120-125.

Zhang, Y. et al. "Electric-Field-Directed Growth of Aligned single-Walled Carbon Nanotubes." Applied Physics Letters, vol. 79, No. 19, Nov. 5, 2001, pp. 3155-3157.

Zhou, P. et al. "Thermomechanical diagnostics of FLIP-CHIP/BGA Structures Using Phase-Shifting Electronic Speckle Pattern Interferometry." EEP, Advances in Electronic Packaging, vol. 26-2, ASME, 1999, pp. 1875-1880.

Cornwell, et al.; "Elastic Properties of Single-Walled Carbon Naonotubes in Compression"; 1997; Dept. of Physics, Florida Atlantic University, Boca Raton FL USA Solid State Communications, vol. 101, No. 8, pp. 555-558.

Iijima S and Ichihashi, "Single-shell carbon nanotubes of 1-nm diameter", Nature 363, 603 (1993).

Baughman R H, Zakhidov A A and de Heer, "Carbon Nanotubes— the Route Toward Applications", W A, Science 297, 787 (2002).

Wong E W, Sheehan P E and Lieber C M, "Nanobeam Mechanics: Elasticity, Strength, and Toughness of Nanorods and Nanotubes", Science 277, 1971 (1997).

Yu M F, Files B S, Arepalli S and Ruoff R S, Tensile Loading of Ropes of Single Wall Carbon Nanotubes and their Mechanical Properties', Phys. Rev. Lett. 84 5552 (2000).

Odom T W, Huang J L, Kim P and Lieber C M, ,"Atomic structure and electronic properties of single-walled carbon nanotubes", Nature 391, 62 (1998).

Wilder J W G, Venema L C, Rinzler A G, Smalley R E and Dekker C, "Electronic structure of Atomically resolved carbon nanotubes", Nature, 391, 59(1998).

J. Li, Q. Ye, A. Cassell, H. T. Ng, R. Stevens, J. Han, M. Meyyappan, "Bottom-up approach for carbon nanotube interconnects", Appl. Phys. Lett., 82, 2491 (2003).

Baughmab R H et al, "Carbon Nanotube Actuators", Science 284, 1340 (1999).

Star A, Lu Y, Bradley K and Gruner G, "Nano Optoelectronic Memory Devices", Nano Lett. 4, 1587 (2004).

J. Lee, H. Kim, SJ Kahng, G. Kim, YW Son, J. Ilm, H. Kato, ZW Wang, T. Okazaki, H. Shonohara, Y. Kuk, "Bandgap Modulation of Carbon Nanotubes by Encapsulated Metallofullerenes", pp. 1005-1008.

Collins P C, Arnold M S and Avouris P, "Engineering Carbon Nanotubes and Nanotube Circuits Using Electrical Breakdown", Science 292, 706 (2001).

Bachtold A, Hadley P, Nakanishi T and Dekker C, "Logic Circuits with Carbon Nanotube Transistors", Science 294, 1317 (2001).

J. Koehne, H. Chen, J. Li, A. Cassell, Q. Ye, H. T. Ng, J. Han, M. Meyyappan, "Ultrasensitive label-free DNA analysis using an electronic chip based on carbon nanotube nanoelectrode arrays", Nanotechnology, 14 , 1239 (2003).

Kong J, Franklin N R, Zhou C, Chapline M G, Peng S, Cho K and Dai H, "Nanotube Molecular Wires as Chemical Sensors", Science 287, 622 (2000).

Li, J, Lu Y, Ye Q, Cinke M, Han J and Meyyapan M, "Carbon Nanotube Sensors for Gas and Organic Vapor Detection", Nano Lett. 3, 929 (2003).

Novak J P, Snow E S, Houser E J, Park D, Stepnowski J L and Mcgill R A, "Nerve agent detection using networks of single-walled carbon nanotubes", Appl. Phys. Lett. 83, 4026 (2003).

Rodney S. Ruoff and Donald C. Lorents, "Mechanical and Thermal Properties of Carbon Nanotubes", Carbon 33, 925 (1995).

M. Fujii, X. Zhang, H. Xie, H. Ago, K. Takahashi, T. Ikuta, H. Abe, T. Shimizu, "Measuring the Thermal Conductivity of a Single Carbon Nanotube", Phys. Rev. Lett. 95, 065502 (2005).

P. Kim,L. Shi,A. Majumdar,and P. L. McEuen, "Thermal Transport Measurements of Individual Multiwalled Nanotubes", Phys. Rev. Lett.87 215502 (2001).

E.Pop, D. Mann, Q. Wang, K. Goodson and H. Dai, "Thermal Conductance of an Individual Single-Wall Carbon Nanotube above Room Temperature", Nano Lett. 6, 96 (2006).

J. Xu, T.S. Fisher, "Enhancement of Thermal Interface Materials with Carbon Nanotube Arrays," International Journal of Heat and Mass Transfer, vol. 49, pp. 1658-1666, (2006).

C.Yu, S. Saha, J. Zhou, L. Shi, A. Cassell, B. A. Cruden, Q.Ngo, J. Li, "Thermal Contact Resistance and Thermal Conductivity of a Carbon Nanofiber", J. Heat. Tran. 2006, 128, 234.

X. W. Wang, H. Hu, X. Xu, "Photo-Acoustic Measurement of Thermal Conductivity of Thin Films and Bulk Materials", ASME, J. Heat Transfer, 123, 138 (2001).

M. S. Dresselhaus, A. Jorio, A.G. S. Filho, G. Dresselhaus, R. Saito, "Raman spectroscopy on one isolated carbon nanotube", Physica B. 232, 15 (2002).

M. S. Dresselhaus, P. C. Eklund, "Phonons in carbon nanotubes", Adv. Phys. 49, 705 (2000).

S. Markutsya, C. Jiang, Y. Pikus, V. Tsukruk, "Freely Suspended Layer-by-layer Nanomembranes: Testing Micrormechanical Properties", pp. 771-780, (2005).

S. D. Brown, P. Corrio, A. Marucci, M. S. Dresselhaus, M. A. Pementa, K. Kneipp, , "Anti-Stokes Raman spectra of single-walled carbon nanotubes", Phys. Rev. B. 61, 5137 (2000).

A. Jorio, R. Saito, J. H. Hafner, C.M. Lieber, M. Hunter, T. McClure, G. Dresselhaus, M. S. Dresselhaus, "Structural (n,m) Determination of Isolated Single-Wall Carbon Nanotubes by Resonant Raman Scattering", Phys. Rev. Lett. 86, 1118 (2001).

JP Sullivan, PD Burrow, DS Newman, K. Bartschat, JA Michejda, R. Panajotovic, M. Moghbelalhossein, RP McEachran, SJ Buckman, "An Experimental and Theoretical Study of Transient Negative Ions in Mg, Zn, Cd, and Hg", pp. 159.1-159.26, (2003).

V. N. Popov, "Carbon nanotubes: properties and application", Mat. Sci. Eng. R, 43, 61, (2004).

A. Bachtold, M. Henny, C. Terrier, C. Strunck and C. Schonenberger, "Contacting carbon nanotubes selectively with low-ohmic contacts for four-probe electric measurements", Appl. Phys. Lett. 73, 274, (1998).

Y. Zhang, T. Ichihashi, E. Landree, F. Nihey and S. Ijima, "Heterostructures of Single-Walled Carbon Nanotubes and Carbide Nanorods", Science, 285, 1719 (1999).

J. Lee, C. park, J.J. Kim, J. Kim, J. W. Park, K. H. Yoo, "Formation of low-resistance ohmic contacts between carbon nanotube and metal electrodes by a rapid thermal annealing method", J. Phys. D. Appl. Phys. 33, 1953 (2000).

S. V. Terekhov, E. D. Obraztsova, A. S. Lobach, V. I. Konov, "Laser heating method for estimation of carbon annotube purity", Appl. Phys. A, 74, 393 (2002).

S. V. Terekhov, E. D. Obraztsova, U. D. Weglikowska, S. Roth, "Calibration of Raman-Based Method for Estimation of Carbon Nanotube Purity", AIP Proc. 685, 116 (2003).

E. Shuir, "1Bimaterial assembly with a low modulus bonding layer at the ends", Journal of Applied Physics, 93, 3657, (2003).

M. M. J. Treacy, T. W. Ebbesen, J.M. Gibson, "Exceptionally high Young's modulus observed for individual carbon nanotubes", Lett Nature, 381, 678, (1996).

Yao, N. and Lordi, V., "Young's Modulus of Single Walled Carbon Nanotubes", J. Appl. Phys., 84(4):1939-1943, (1998).

Hernandez, E., Gose, C., Bernier, P., and Rubio, A., "Elastic Properties of c and bxcynz Composite Nanotubes", Phys. Rev. Lett., 80(20):4502-4505, (1998).

Krishnan, A., Dujardin, E., Ebbesen, T.W., Yianilos, P.N., and Treacy, M.M.J., "Young's Modulus of Single Walled Nanotubes", Phys. Rev. B. 58(20):14013-14019, (1998).

P. Poncharal, Z. L. Wang, D. Ugarte and W. A. de Heer "Electrostatic Deflections and Electromechanical Resonances of Carbon Nanotubes" Science, 283, 1513 (1999).

Gaillard, J., M. Skove, and A.M. Rao, 2005, "Mechanical properties of chemical vapor deposition-grown multiwalled carbon nanotubes", Applied Physics Letters, vol. 86, No. 23 (2005).

Wei, C. and D. Srivastava, 2004, "Nanomechanics of carbon nanofibers: structural and elastic properties", Applied Physics Letters, vol. 85, No. 12, pp. 2208-2210 (2004).

Salvetat JP et al, "Elastic Modulus of Ordered and Disordered Multi-Walled Carbon Nanotubes", Adv. Mater. 11(2):161-165, (1999).

A. Cao, P. Dickrell, W. G. Sawyer, M. Ghasemi-Nejhad and P. Ajayan, "Super compressible foam like carbon nanotube films", Science, 310, 1307 (2005).

Zhou, X., Zhou, J.J., and Ou-Yang, Z.C., "Strain Energy and Young's Modulus of Single-Wall Carbon Nanotubes Calculated From Electronic Energy-Band Theory", Phys. Rev., B, 62(20):13692-13696, (2000).

Ru, C.Q., "Effective Bending Stiffness of Carbon Nanotubes", Phys. Rev. B. 62(15):9973-9976, (2000).

M. F. Yu et. al., "Strength and Breaking Mechanism of Multiwalled Carbon Nanotubes Under Tensile Load", Science, 287, 637 (2000).

T. Kuzumaki et. al., "Dynamic measurement of electrical conductivity of carbon nanotubes during mechanical deformation by nanoprobe manipulation in transmission electron microscopy", Appl. Phys. Lett. 85, 1250 (2004).

M. Nishio et. Al., Buckling Test under Axial Compression for Multiwall Carbon Nanotubes, Jpn. J. Appl. Phys. 44, L1097 (2005).

Govindjee, S. and Sackman, J.L., "On the Use of Continuum Mechanics to Estimate the Properties of Nanotubes", Solid State Comm., 110(4):227-230, (1999).

Harik, V.M., "Ranges of Applicability for the Continuum Beam Model in the Mechanics of Carbon Nano-Tubes and Nano-Rods", Solid State Comm, 120(331-335), (2001).

Lourie, O., Cox, D.M. and Wagner, H.D., "Buckling and Collapse of Embedded Carbon Nanotubes", Phys. Rev. Letters, 81(8): 1638-1641, (1988).

Falvo, M.R., et al, "Bending and Buckling of Carbon Nanotubes Under Large Strain", Nature, 389 (6651): 582-584, (1997).

Ru, C.Q., "Effect of van der Waals Forces on Axial Buckling of a Double-Walled Carbon Nanotube", J.Appl.Phys., 87(10):7227-7231, (2000).

Ru, C.Q., "Column Buckling of Multi-Walled Carbon Nanotubes with Interlayer Radial Displacements", Phys. Rev., B, 62(24):16962-16967, (2000).

Ru, C.Q., "Degraded Axial Buckling Strain of Multi-Walled Carbon Nanotibes due to Interlayer Slips", J. Appl. Physics, 89(6):3426-3433, (2001).

CY Wang, C-Q Ru, A Mioduchowski, "Axially Compressed Buckling of Pressured Multiwall Carbon Nanotubes", pp. 3893-3911, (2002).

Ru, C.Q., "Elastic Buckling of Single Walled Carbon Nanotube Ropes Under High Pressure", Phys. Rev., B. 62(15):10405-10408, (2000).

B. A. Cruden, A. M. Cassell, Q. Ye, and M. Meyyappan, "Reactor design considerations in the hot filament/direct current plasma synthesis of carbon nanofibers", J. Appl. Phys., 94, 4070, (2003).

J. Li, R. Steven, L. Delzeit, H. T. Ng, A. Cassell, J. Han and M. Meyyappan, "Electronic properties of multiwalled carbon nanotubes in an embedded vertical array", Appl. Phys. Lett. 2002, 81, 910 (2002).

H. Cui, S. V. Kalinin, X. Yang and D. H. Lowndes, "Growth of Carbon Nanofibers on Tipless Cantilevers for High Resolution Topography and Magnetic Force Imaging", Nano Lett. 4, 2157 (2004).

I. C. Chen, L. H. Chen, X. R. Ye, C. Daraio, S. Jin, C. A. Orme, A. Quist and R. Lal., "Extremely sharp carbon nanocone probes for atomic force microscopy imaging", Appl. Phys. Lett. 88, 153102 (2006).

E. Suhir, "Analysis of Interfacial Thermal Stresses in a Tri-Material Assembly", Journal of Applied Physics, 89, 3685 (2001).

* cited by examiner

METHOD AND APPARATUS FOR EVALUATION AND IMPROVEMENT OF MECHANICAL AND THERMAL PROPERTIES OF CNT/CNF ARRAYS

CROSS REFERENCE TO RELATED APPLICATIONS

This application claims priority to U.S. provisional patent application Ser. No. 60/862,664, filed Oct. 24, 2006, which application is incorporated herein in its entirety by this reference thereto.

BACKGROUND OF THE INVENTION

1. Field of the Invention

The invention generally relates to the mechanical properties, material quality, mechanical behavior and bonding strength of carbon nanotoube and carbon nanofiber-based materials. More specifically, the invention relates to structures for thermal management of integrated circuit (IC) devices.

2. Discussion of the Prior Art

Since their discovery, carbon nanotubes (CNTs) and carbon nanofibers (CNFs) have attracted interest of a significant number of researchers and engineers. CNTs possess unique structure, as well as extraordinary mechanical, electrical, and optical properties. There are also numerous patents and patent applications that have been issued or filed in the area in question. It has been shown that CNTs can be used as optoelectronic devices, field effect transistors (FET), and sensors. It has also been found that thermal conductivity of CNTs can be exceptionally high: even higher than that of a diamond. Numerous studies, primarily theoretical, have been recently conducted to evaluate the thermal performance of CNTs and their applicability for heat removal in integrated circuits (IC). The thermal conductivity of single wall carbon nanotubes (SWCNT) was investigated using various simulation techniques, such as molecular dynamics (MD) simulation, non-equilibrium simulation, and the force field theory. Although the obtained data are inconsistent and show significant discrepancy, the data nonetheless confirmed that the expected level of CNT thermal conductivity could be quite high: 6,000 W/m·K, 375 W/m·K, 1,600 W/m·K, and 2,980 W/m·K, i.e. much higher than that of most of existing materials. There exists, therefore, significant interest in using CNTs as thermal interface materials (TIMs) for thermal management of ICs, and there exists a significant incentive in using CNTs and CNFs as TIMs.

As for the experimental studies, it has been found that the thermal conductivity of individual multiwall carbon nanotubes (MWCNT) at room temperature could be as high as 3,000 W/m·K. This result is within the region of theoretical predictions. For SWCNT dense-packed ropes, however, a rather low value of 35 W/m·K was obtained for mat samples. A thermal conductivity level of 150 W/m·K was reported by Shi et al for SWCNTs in a bundle, and having an average diameter of 10 nm. Theoretically, the thermal conductivity of MWCNTs should be lower when compared to SWCNTs. Indeed, some experiments showed that the thermal conductivity of aligned MWCNTs could be as low as 12-17 W/m·K. A somewhat higher value of 27 W/m·K was obtained by several other groups.

In general, research do date indicates that, although the thermal conductivity of CNT bundles could be significantly lower than the theoretical predictions (1,600-6,600 W/m K) and the conductivity of single CNTs there is, nonetheless, a clear indication that CNTs can have a higher conductivity than the regular TIMs that are currently used for IC cooling, which is only about 3-7 W/m·K. With all this information available, one can conclude that, although there is both a considerable interest in the use of CNTs and CNFs as TIMs and a significant incentive for doing that, there is still a long way to go until these devices are developed to an extent that they could become products, i.e. where they are commercially attractive, functionally and mechanically reliable, and environmentally durable.

It is clear also that, to come up with a feasible device, one should be able to develop a viable and a reliable product. To do that, one should know the major mechanical/physical characteristics of the CNT/CNF material.

Figure 1:
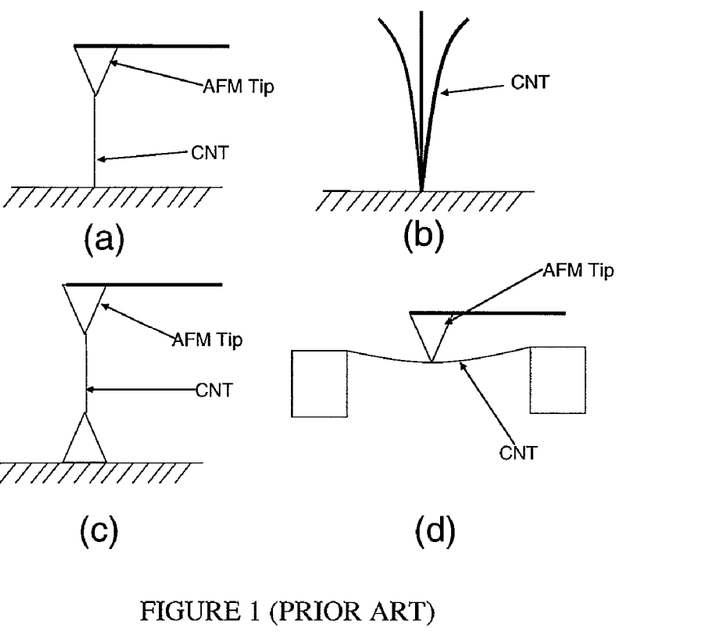
FIG. 1 is a schematic description of four types of conventional Young's modulus measurement methods for individual CNTs (prior art)
Figure 2:
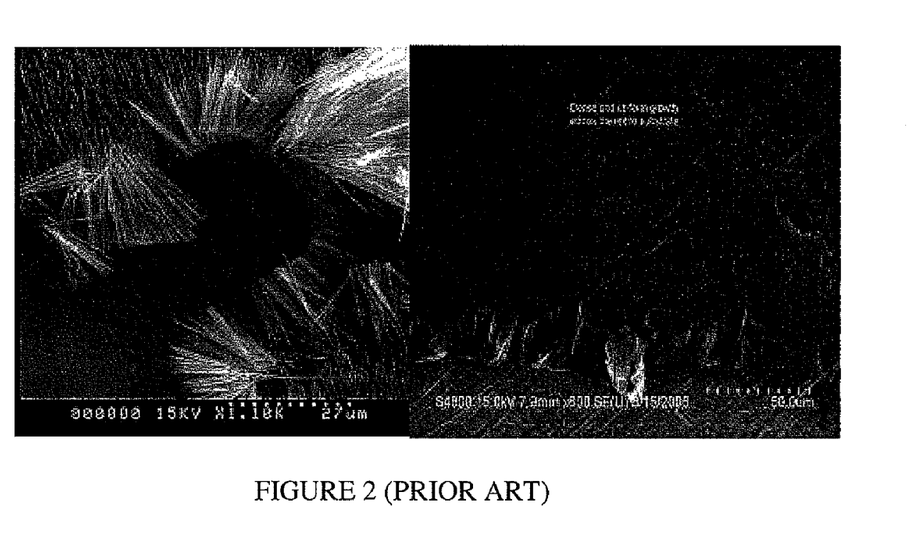
FIG. 2 is a microphotograph of a typical prior art scanning electronic microscopy tilt view and top view of the PECVD synthesized carbon nanofiber and TECVD synthesized nanofiber array synthesized on Cu substrate (prior art)

Young's modulus (YM) is an important material characteristic of the CNT and CNF material, and therefore substantial effort is dedicated to its evaluation. The YM of CNTs, such as those shown with respect of FIG. 1, was measured by generating a thermal vibration of CNTs and using high resolution tunneling electron microscope (HRTEM). The mechanical behavior of individual CNFs was investigated using the nanoprobe manipulation method shown, for example, with respect to FIG. 2. It has been found that the YM of a CNT/CNF might depend on its diameter and, based on reported data, might change from 2 TPa to 200 GPa, when the CNT diameter changes from 5 nm to 40 nm. This information agrees with the experimental data that were obtained using the external oscillated electrical field assisted HRTEM. It has been found that the YM of the CNTs decreases exponentially with an increase in the CNT diameter. Carbon nanofibers (CNFs) produced by PECVD are characterized by much larger diameters (about 100 nm). Because of that, and also because of the far-from-ideal bamboo-like morphology of the CNFs, their effective Young's modulus (EYM) is expected to be much lower than that of the CNTs.

In this connection, it should be emphasized that there is a significant incentive in evaluating the effective Young's modulus (EYM) of the CNT/CNF array. The EYM characterizes, in a phenomenological fashion, the mechanical behavior of a CNT/CNF array treated as a, sort of, continuous material layer. The EYM might be quite different from the actual, micro- or nano-scale YM that could be found based on the testing of an individual CNT or a CNF. At the same time it might, and typically is, sufficient to have the most accurate information of the EYM to carry out a practical design of a CNT/CNF-based TIM. Therefore, in this disclosure the inventors herein treat the CNF array (CNFA) brush as a continuous elastic strip. The elastic response of a continuous, homogeneous, and isotropic elastic medium depends on two constants i.e. YM and Poisson's ratio, or on the two Lame constants, which are derivative of the above two constants. While the Poisson's ratio changes in relatively narrow limits, the YM and the EYM might be quite different for CNT/CNF materials obtained by using different synthesis methods. At the same time it is well known that it is the YM, and not the Poisson's ratio (unless the material exhibits very unusual mechanical behavior), that plays the most important role in the mechanical behavior and performance of materials.

Although many phenomena of the CNT/CNF materials behavior can be adequately described and explained only on the basis of quantum mechanics, it is often assumed that theory-of-elasticity, and even engineering mechanics methods, can be successfully employed to evaluate the YM of the CNT/CNF materials. There is an obvious incentive for the development of a practical methodology for the evaluation of the EYM of vertically aligned PECVD-synthesized CNFA and CNTA. In this disclosure, the inventors herein show how this could be done on the basis of the measured compressive-force vs. axial-displacement in the post-buckling mode.

There are several reasons why the axial displacements should be large enough to ensure that the CNFA behaves in the post-buckling mode conditions. First, the force-displacement relationships in the post-buckling mode can be obtained in a wide range of measured forces and displacements. Second, exact solutions exist (Euler's elastica) for the evaluation of the highly geometrically nonlinear bending deformations of flexible rods (beams). By treating CNFs as nonlinear beams/wires, one can use elasticasolutions to predict the EYM from the experimentally obtained force-displacement relationship. If the material exhibits nonlinear stress-strain relationship, i.e. if the EYM is stress dependent, then this dependency could be obtained as a suitable correction to the YM value obtained on the basis of the elastica solution. Finally, it is important that the interfacial pressure does not change significantly with the change in the axial displacements of the CNFA. This indeed takes place when the compressed CNFA is operated in the post-buckling condition. Because CNFs are intended to perform in the post-buckling modes in many practical applications, the evaluation of their behavior in such a mode enables one to obtain valuable information for these structural elements under in-use conditions.

The ability to evaluate the bonding, i.e. adhesive, strength of the CNT/CNF array to its substrate is another important problem in making a CNT/CNF-based TIM device into a commercial product. Satisfactory adhesion of the CNF array (CNFA) to its substrate is critical for making the CNF-based technology practical. Accordingly, there is an incentive for the development of an easy-to-use and effective method for the evaluation of such an adhesion. The adhesion strength of a single CNF to its substrate was addressed qualitatively, apparently for the first time, by Cui et al and by Chen et al. This was done in connection with the use of PECVD synthesized CNFs as probe tips in the atomic force microscopy imaging equipment. In the experiments described by these investigators, individual CNFs were directly grown on tipless cantilevers. In the reported observation, the CNF-probe was operated on a continuous scan mode for eight hours. No degradation in image resolution was observed. The CNFA is disclosed herein consists of billions of CNFs. The obtained information characterizes the performance of an ensemble of a plurality of CNFs. To translate the obtained experimental data into corresponding shearing stresses, one has to develop an analytical stress model that enables one to calculate the magnitude and the distribution of the interfacial shearing stress from the measured given, i.e. given, external force. In addition there is a need for designing a special test vehicle for the evaluation of the shearing off strength of the CNT/CNF structures in question. In the invention disclosed herein, the inventors teach how the maximum effective shear stress-at-failure for a CNFA fabricated on a thick Cu substrate could be determined and, if necessary, specified. As in the case of the Young's modulus, the inventors herein both use the term "effective" to emphasize that a plurality of CNFs and treat the CNFA "brush" as a sort of a continuous bonding layer. This approach enables one to use an analytical stress model that was developed for the evaluation of the interfacial shearing stress in an assembly with a continuous bonding layer. The developed model is a modification of the models that were suggested earlier for the evaluation of the interfacial thermally induced stresses in thermally mismatched assemblies

SUMMARY OF THE INVENTION

A method and apparatus for the evaluation and improvement of the mechanical and thermal properties of carbon-nanotube (CNT) and carbon nanofiber (CNF) arrays grown on a substrate is disclosed. The Young's modulus of a CNT/CNF material is measured by applying an axial compressive force on the CNT/CNF array and measuring the applied forces and the induced displacements. Also disclosed are the evaluation of the nonlinear stress-strain relationship of the CNT/CNF material, increasing of the Young's modulus and decreasing the thermal resistance by application of a compressive load, the application of rapid thermal annealing to improve the quality of the CNT/CNF material and to reduce the interfacial thermal resistance, improvement of the bonding strength of the CNT/CNF array to a substrate, evaluation of the bonding strength of the CNT/CNF array to a substrate, evaluation of the shearing force at failure, and an analytical stress model that enables one to predict the interfacial shearing stress from the measured force.

DETAILED DESCRIPTION OF THE INVENTION

A method and apparatus for the evaluation and improvement of the mechanical and thermal properties of carbon-nanotube (CNT) and carbon nanofiber (CNF) arrays grown on silicon or metal, e.g. copper, substrates is disclosed. The Young's modulus of a CNT/CNF material is measured by applying an axial compressive force to the CNT/CNF array, and measuring the applied forces and the induced displacements. Also disclosed are the evaluation of the nonlinear stress-strain relationship of the CNT/CNF material, increasing of the Young's modulus and decreasing the thermal resistance by application of a compressive load, the application of rapid thermal annealing to improve the quality of the CNT/CNF material and to reduce the interfacial thermal resistance and possibly improve the adhesive bonding strength of the CNT/CNF array to its substrate as well, evaluation of the bonding strength of the CNT/CNF array to a substrate, evaluation of the shearing force at failure, and an analytical stress model that enables one to predict the interfacial shearing stress from the measured force. The inventors also disclose that some of the results provided herein can be used to standardize the manner in which Young's moduli of CNT/CNF materials are evaluated, as well as the way that the strength of adhesive strength of the CNT/CNF arrays to their substrates is assessed.

Specifically, the invention described herein is of particular application with respect to the CNT/CNF described in U.S. Pat. No. 7,109,581, entitled *System and Method Using Self-Assembled Nano Structures in the Design and Fabrication of an Integrated Circuit Micro-Cooler*, assigned to a common assignee, and which is incorporated herein in its entirety by reference this reference thereto for all the useful material it may contain. Briefly described, a plurality of individually separated, rod-like nano-structures are disposed between the heat sink surface and the heat generating surface, typically at a density of between 15% and 40% coverage density. A thermally conductive material is disposed within interstitial voids between the rod-like nano-structures. A micro-cooler device is therefore manufactured by using a shallow cavity in a mounting surface of a heat sink body, growing rod-like nano-structures within the shallow cavity, depositing a thermally conductive material in interstitial voids between the rod-like nano-structures, and providing a protrusion of the edges or ends of the rod-like nano-structures from opposite surfaces of the structure. Such nano-structures therefore include CNTs, CNFs, and nanowires.

The methodology for measuring Young's modulus of CNT/CNF arrays determines if the mechanical properties of the CNT/CNF arrays are suitable as thermal interface materials. Accordingly, the Young's modulus is measured based on the following procedures:

(1) The CNF/CNT array (FIG. 3) that is comprised of CNTs/CNFs 320 grown from a substrate 330 is placed between a load surface 310 and a parallel surface 340. The substrate 330 is placed on the lower anvil 340, while the upper anvil 310 is automatically and thoroughly controlled to approach the surface of the CNF/CNT array and apply forces 350 uniformly. This can be achieved by using a commercially available equipment-table version of, for example, the Instron tester-Model 5542. The Instron equipment, e.g. the table version, can be used to evaluate the applied force.

(2) A non-contact determination of the displacement of the CNFA and CNTA is achieved by using measuring equipment such as, but not limited to, the Capacitec equipment. The Capacitec equipment can be used to evaluate, in a non-contact fashion, the induced axial displacement. By using the combination of devices of steps (1) and (2), it is possible to measure the force versus displacement with high resolution and, owing to that, to calculate the effective Young Modulus (EYM) with high accuracy.

(3) Based on the developed predictive model developed for the flexible rod, one can obtain the T/Te vs. δ/l relationship, where T is the compressive force, $T_e$ is the calculated buckling force, assuming that an individual CNF, could be idealized as a cantilever rod, δ is the axial displacement of an individual CNF and l is its length. Accordingly, one can calculate the YM from the relationship above. However, in accordance to the disclosed invention, and as a result of measuring the force-displacement relationship, it is possible to obtain the relationship between the actually applied force T and the relative displacement δ/l. Based on this relationship, assuming the YM ($E_0$) at low strain of the CNF array is constant, is directly calculated according to Ru, C. Q., *Effect of van der Waals Forces on Axial Buckling of a Double-Walled Carbon Nanotube*, J. Appl. Phys., 87(10):7227-7231 (2000). However, if the nonlinearity of the YM of the CNFs array is considered, the YM may be obtained as:

$$E \approx E_0 + \gamma \sigma \quad (1)$$

Figure 4:
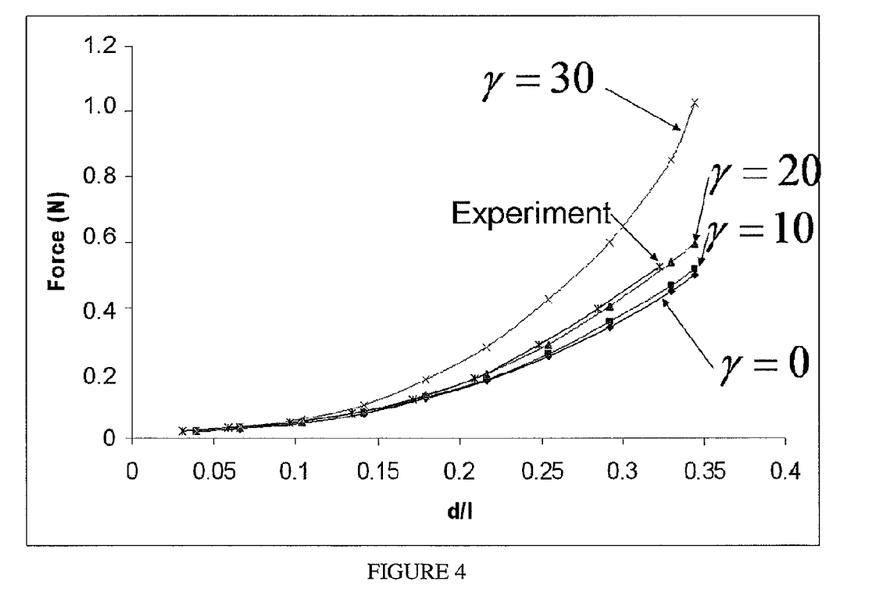
FIG. 4 is a diagram of the simulated relationship between the applied force T and the displacement-to-length ratio $\delta/l$ corresponding to different nonlinear coefficient.

Where, σ is the compressive stress and γ is the nonlinear factor, which are both obtained from the directed compressive stress vs. displacement relationship. To determine the most fit γ value, a series of stress vs. displacement curves based on various γ values are generated, as shown in FIG. 4. Such a plot enables one to approximate, i.e fit, the experiment results to the theoretically developed curves, and thereby obtain appropriate γ values that result in the most reasonable agreement with the experimental and the theoretical data. Then, these γ values are used to calculate the Young's moduli.

Figure 3:
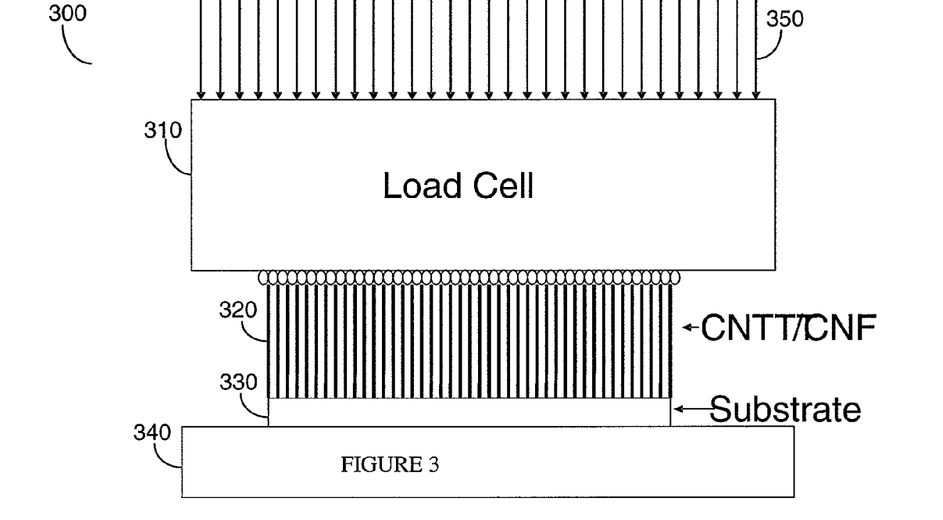
FIG. 3 is a schematic drawing of an apparatus for measuring the Young's modulus of the CNT/CNF array according to the invention.

(4) With reference to FIG. 4, there are shown some simulation results for different values of the parameter γ of nonlinearity, along with experimentally obtained curves for a particular specimen, such as that shown with respect to FIG. 3. As evident from the plotted data, the theoretical curve with the parameter of nonlinearity of γ=20 satisfactorily matches the experimentally obtained curve. Hence, it is this γ value that could be used to evaluate the EYM for a CNT/CNF array.

Figure 5A:
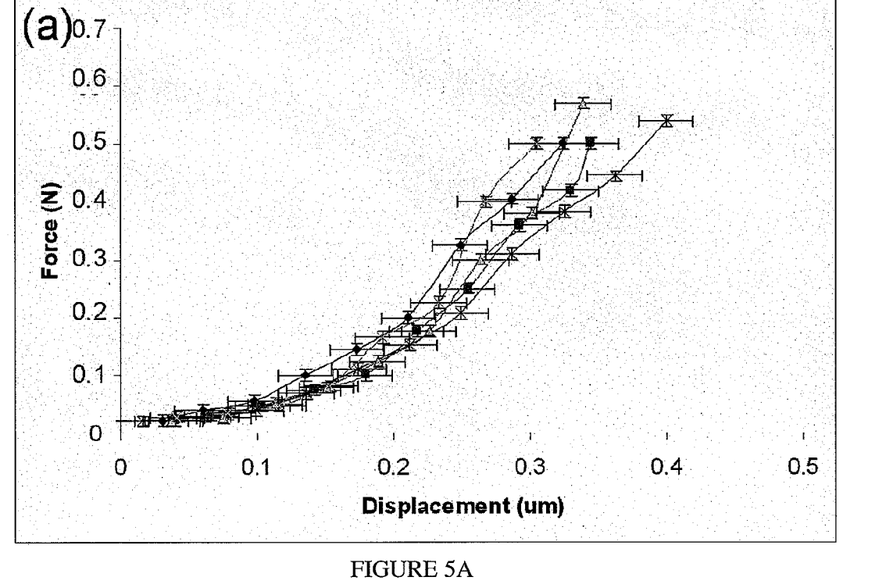
FIG. 5A shows a measured compressive force as a function of the $\delta/l$ ratio for five samples taken from the same wafer.
Figure 5B:
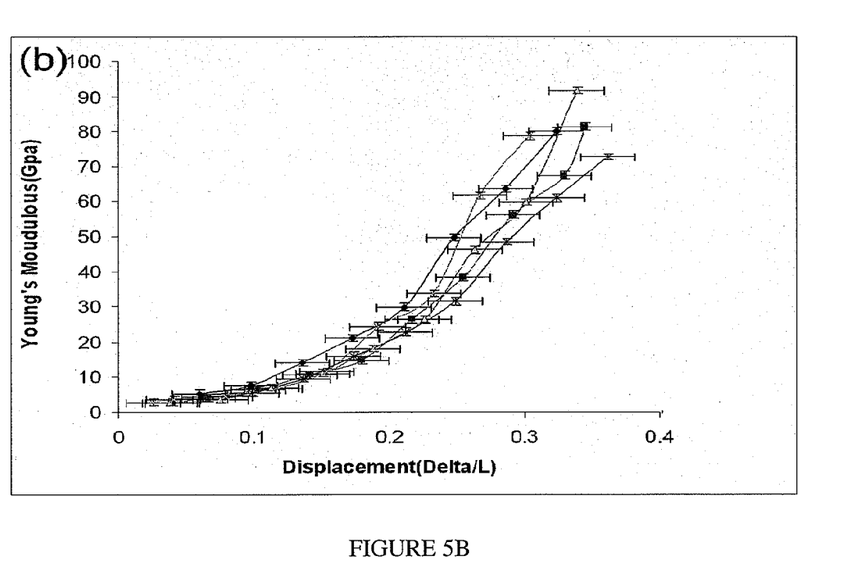
FIG. 5B shows a calculated YM of for five samples taken from the same wafer based on the measured compressive force of FIG. 5A.
Figure 6:
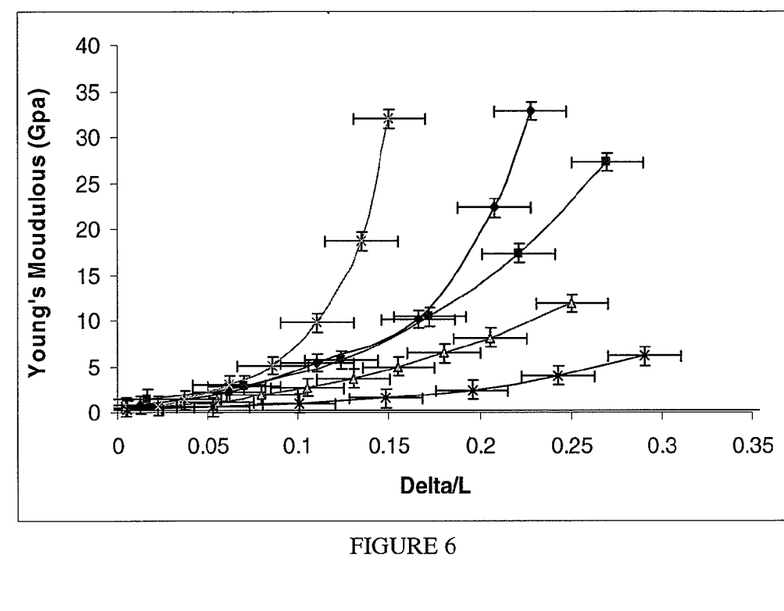
FIG. 6 is a diagram of the calculated Young's modulus vs. $\delta/l$ ratios for samples taken from different runs (different growth conditions)

(5) This testing method is sufficiently sensitive and accurate enough to separate the mechanical properties of the CNT/CNF materials. As a qualification method, a CNF/CNT array synthesized by the same grow condition should be consistent with any other CNF/CNT array. The deviation among the samples should fall into the error bar region of the testing results as can be seen for the forces and the Young's modulus with respect of FIGS. 5A and 5B. As can be seen in FIG. 5B, a 30% lateral displacement of the CNT array corresponds to a Young's modulus of 90 Gpa. For samples synthesized with different conditions, the measured Young's modulus of the CNFs samples could be well separated, as shown with respect to FIG. 6, and it could be used to distinguish the quality of the CNF/CNTs. The CNF/CNT with better quality would possess larger Young's modulus and better mechanical properties. These data indicate that different growth conditions result, in effect, in considerably different materials. The CNF/CNT with good qualities possesses better mechanical properties and a larger Young's modulus.

Figure 8:
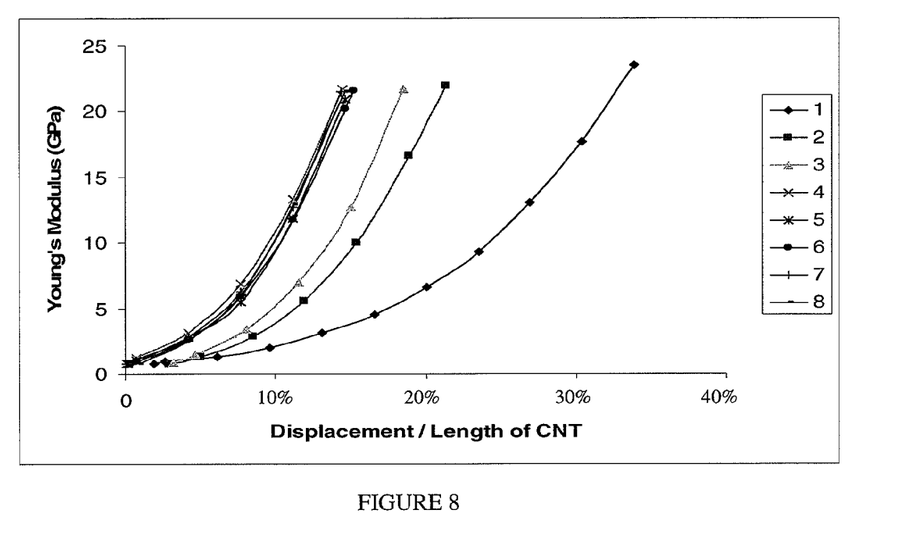
FIG. 8 shows plots of the Young's modulus of individual carbon nanofibers in the array and the whole carbon nanofiber array after compressing the surface of PECVD synthesized carbon nanofiber array.

By applying repetitive compression on the surface of the CNF arrays, one finds out that the Young's modulus of the CNF arrays gets saturated (see FIG. 8). The surface of the CNF array becomes uniform after the compressive cycles.

Figure 9:
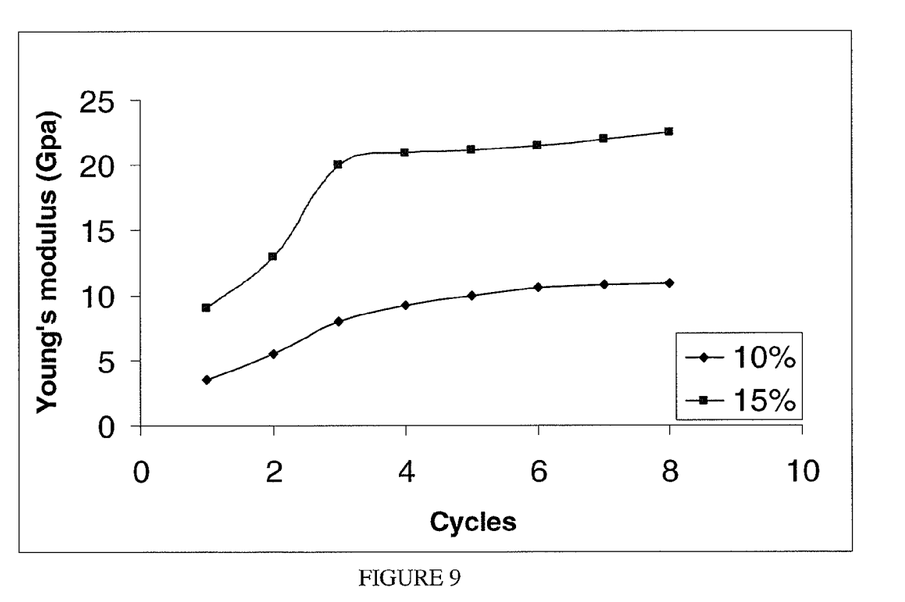
FIG. 9 shows plots of the Young's modulus of CNF array and of the individual CNFs begin to increase at different displacement positions.

The Young's modulus of the CNF array increases as shown, with respect to FIG. 9. This method can be used to improve the mechanical properties of the CNF/CNT array.

Due to the fact that the EYM of the CNT array gets saturated when the CNTs are compressed a few times, the inventors further investigated this phenomenon by studying its effect on the thermal performance of the CNT array. Specifically, but by no means of limitation, samples from the same wafer were prepared, and the thermal resistance of ten samples was measured directly with the set-up used described above. For the other ten samples, a 50 gf compressive force was applied to the surface of CNTs array eight times for each sample, as shown in FIG. 3. The thermal resistances of these samples were improved (see FIG. 10). Because the thermal properties measurement method used is precise enough to distinguish the thermal resistance difference as small as 0.01 $cm^2 \cdot K/W$, the improved thermal resistance caused by the repeatedly applied compressive force is real and not caused by the error reading of the experiment.

Figure 7A:
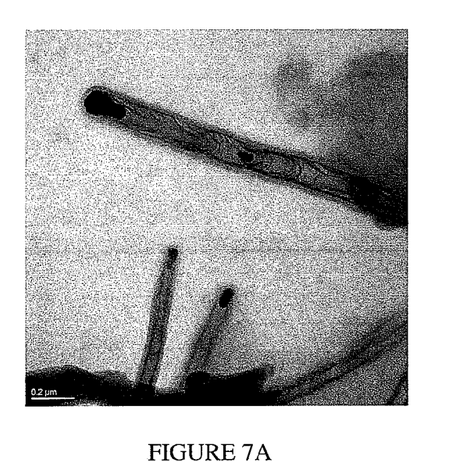
FIG. 7A is a high-resolution transmission electron microscopy (HRTEM) image of the general structure view of CNFs synthesized at lower temperature.
Figure 7B:
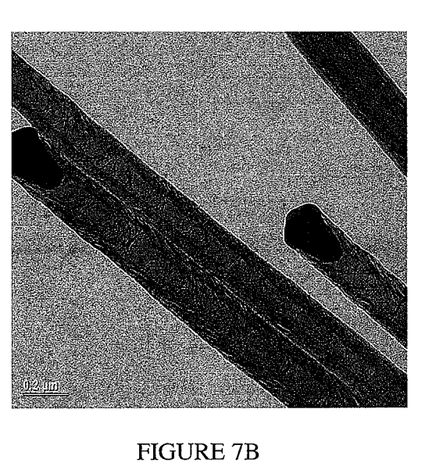
FIG. 7B is an HRTEM image of the general structure view of CNFs synthesized at higher temperature.

In addition, with series of samples tested the statistical results are sufficient to prove the improvement of thermal performance of these CNT arrays. The improvement of the thermal performance of the CNTs array could be attributed into two factors. Generally, it is accepted that the PECVD grown CNTs would normally have a bamboo structure, such as those shown with respect to FIG. 7, and this unique structure increases the amount of photon scattering. It decreases the thermal performance of the CNTs. However, due to continuous compression of the CNTs array, it is likely that the force squeezes the spaces between the bamboo structures and finally the CNTs get stiffer. The stiffer mechanical structure of the CNTs array help in studying the fact that the effective YM of CNT array saturated at a certain limit which, in turn, reflected that the thermal resistance of the CNTs array is reduced. With respect to FIGS. 7A and 7B, the bamboo-like graphitic structure and the shape of the Ni tip are clearly observed. The quality of the CNF shown in FIG. 7B is better than the quality of the CNF shown in FIG. 7A. The Young's Modulus of the CNFs array is measured to be higher for the samples on the right (FIG. 7*b*) than the samples on the left (FIG. 7*a*).

Another factor that helps to reduce the thermal resistance is the surface roughness. It is well accepted that the interface resistance could be a crucial condition of using the CNTs as an interfacial heat dissipation material. The interface resistance strongly affects the thermal performance of the whole CNT array. The interface resistance is affected by several factors, such as the density of the CNT, contact area, contact material, and so on. Besides of this, the length uniformity of the CNTs in the array is another important factor. It reflects the actual amount of CNTs in contact with the load cell. With more CNTs in contact with the load cell, the effective YM is definitely larger and the thermal resistance is reduced as well. Thus, with a small compressive force applied onto the CNTs several times the surface of the CNTs the array is more uniform than before and results in the phenomena explained in more detail above.

Rapid thermal annealing (RTA) is used to improve the adhesion of the CNF/CNT array with its substrate, and to improve the thermal and electrical properties of the CNF/CNT array accordingly. Therefore, in accordance with the disclosed invention, first the CNF/CNT array is moved into a chamber at room temperature and $N_2$ and Ar are pumped into the chamber to achieve an oxygen free atmosphere for a period of, for example, five minutes. Second, the CNF/CNT array is annealed at 800° C.-1050° C. in a 30-second ramping. When the CNF/CNT array reaches the desired temperature, it is soaked for a period of, for example, one minute in $N_2$ and Ar atmosphere. With an increasing RTA temperature with the same RTA process procedures described above, the thermal resistances of the CNF/CNT array is reduced accordingly. During the RTA process, the structure of the CNTs improves during the high temperature processes which, in turn, reduces the thermal resistance of the CNTs samples. During the synthesis of the CNTs, amorphous carbon is generated as a side product of the CNTs. Generally, it is well known that the CNTs generated at a higher temperature have a better graphitic structure and the amount of the amorphous carbon is reduced as well. With this post process at a higher temperature than the growth temperature of the CNF/CNT array, for example a growth temperature of 700° C., a portion of the amorphous carbon on the CNTs is transferred into graphitic layer structure and the already existing graphitic layer of carbon is better crystallized. Due to the fact that the thermal conductivity of the graphitic layer structure is higher than the amorphous carbon, better thermal performance for samples with more graphitic structure is achieved.

Figure 10:
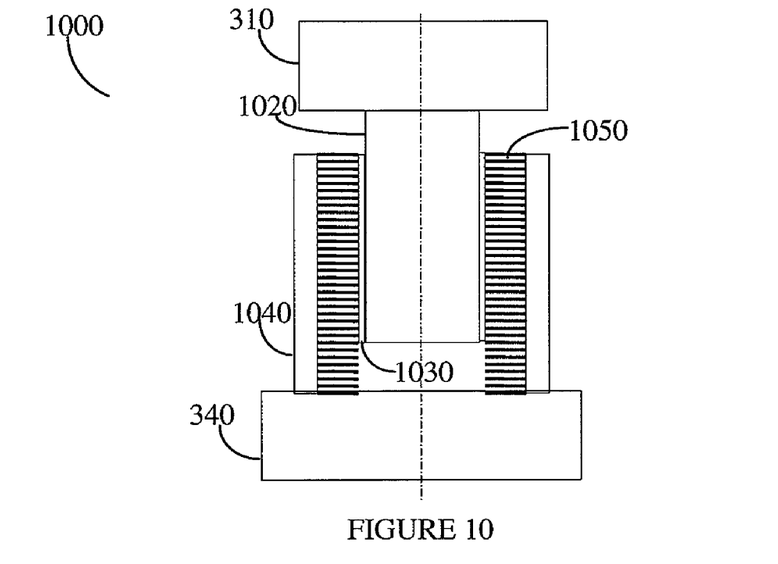
FIG. 10 is a schematic diagram of the sample assembly used to evaluate the adhesion strength of the PECVD synthesized CNF array or TECVD synthesized CNT array to their substrates.

The methodology to measure the adhesion strength of the CNT/CNF arrays is considered as a standard to qualify the mechanical properties of the CNT/CNF arrays as thermal interface material. The adhesion strength of the CNF/CNT array to its substrate is evaluated, in accordance with the disclosed invention, having the following procedure and with reference to FIG. 10:

(1) A central block 1020 is created of, for example a copper plate having exemplary and non-limiting dimensions of 20 mm×20 mm×1 mm;

(2) A copper foil 1030 having a size of, for example, 20 mm×10 mm, is placed on, and pressed onto, the central block 1020 so that the edges of the foil 1030 have the same boundary as the central copper block 1020;

(3) Two identical CNT array 1050 samples grown on a copper substrate, having exemplary and non-limiting dimensions of 20 mm×20 mm×1 mm, are pressed against the copper foil 1030. Typically, only half of the surface of the CNT array 1050 is actually in contact with the copper foil 1030 and able to provide adhesion.

(4) The test specimen is placed on the anvil 340, and the anvil 310 with the load cell is lowered to approach the copper central block 1020, as shown with respect to FIG. 10. Once the load cell 310 is in contact with the central block 1020, the forces applied and the corresponding displacements are recorded, as explained in more detail above with respect to FIG. 3. The copper foil 1030 should be strong enough to hold the top surface of the CNT array 1050 in place. The force applied to the sample increases until it reaches the failure point. At this point, the CNT 1050 is sheared off from the substrate 1040. If the test specimen is ideally assembled, both CNT arrays 1050 would simultaneously be separated from the central block 1050 with the CNT sheared off from the substrate 1040. In reality, however, only one CNT array interface is typically broken.

Figure 11:
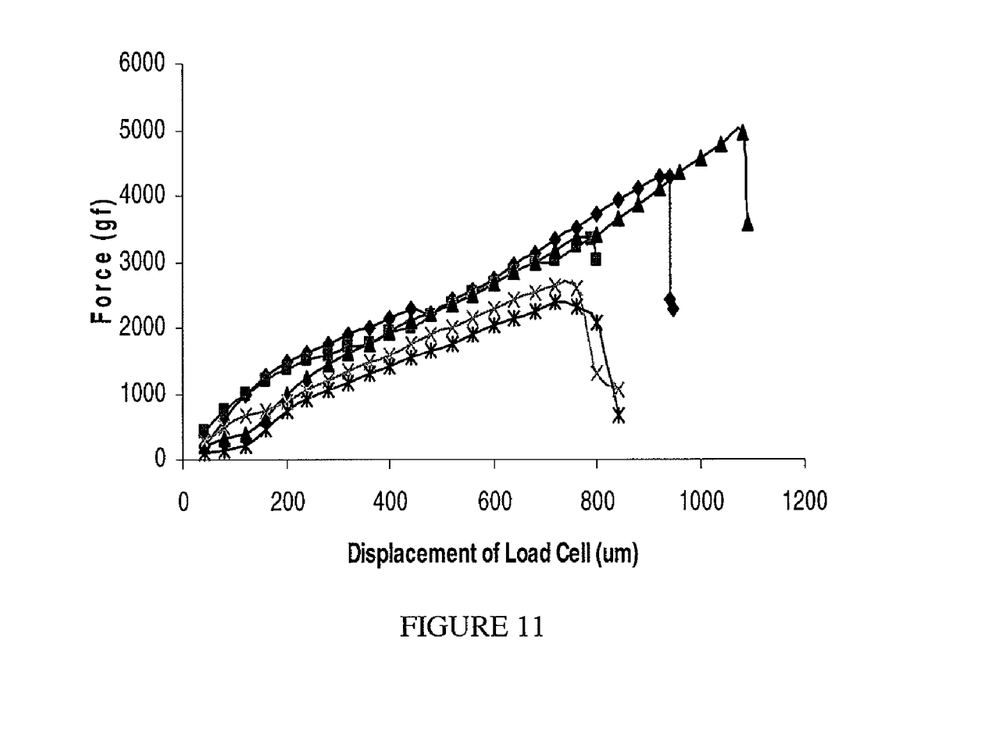
FIG. 11 is a diagram showing the displacement at failure that can be used as a suitable criterion of the adhesion strength of the CNF and CNT array to their respective substrates.

The force-at-failure varies from sample to sample. The most important source of uncertainty is the actual percentage of the contact area between the CNTs in the CNTA with copper foil. If the CNTA is not attached well to the copper tape, the CNTs are not deformed and are not sheared off from the substrate, as shown in FIG. 12. Clearly, with more CNTs in contact with the copper foil, the force holding the CNTA is larger and, as a result, the shear off force increases to a higher value. As one can see from FIG. 11, the maximum force-at-failure varies from 2 kg to 5 kg, depending on how many CNTs are in contact with the copper foil. With reference to FIGS. 12A-12D, exemplary and non-limiting microphotographs of test samples at the failure site, corresponding to the 5 Kg case, are shown. It is clearly observable that about 80% of CNTs were in contact with the copper foil.

The following is an exemplary and non-limiting discussion of the methods used to calculate the shearing pressure from the forces applied in accordance with the embodiments of the disclosed invention. For the well designed configuration used in the inventors' experiment (FIG. 8), to calculate the bi-material shear stress, let a bi-material assembly be subjected to a shearing force $\hat{T}$. The objective of the analysis that follows is to evaluate the magnitude and the distribution of the interfacial shearing stress, $\tau(x)$, from the measured force $\hat{T}$. We proceed from the following approximated formulas for the interfacial longitudinal displacements for the assembly components #1 and #2:

$\hat{T}$ is the force acting in the cross-section x of the assembly, $\tau(x)$ is the shearing stress acting in the same cross-section, $$\lambda_1 = \frac{1-v_1}{E_1 h_1}, \lambda_2 = \frac{1-v_2}{E_2 h_2} \quad (2)$$

are the axial compliances of the assembly components, $h_1$ and $h_2$ are their thicknesses, $E_1$ and $E_2$ are Young's moduli of the component materials, $v_1$ and $v_2$ are Poisson's ratios, $$\kappa_1 = \frac{h_1}{3G_1}, \kappa_2 = \frac{h_2}{3G_2} \quad (3)$$

are the interfacial compliances of the assembly components, $$G_1 = \frac{E_1}{2(1+v_1)}, G_2 = \frac{E_2}{2(1+v_2)} \quad (4)$$

are the shear moduli of the component materials, and L is the assembly length, the origin of the coordinates x is at cross-section where the force $\hat{T}$ is applied. The first terms in the right parts of the formula (A-1) are due to the forces T(x) and are evaluated based on the Hooke's law. The second terms account for the fact that the interfacial shearing displacements are somewhat larger than the displacements of the inter points of the given cross-section. For the starting point, $$\kappa_0 = \frac{h_0}{\varepsilon_0} \quad (5)$$

is the interfacial compliances of the bond layer, $$G_0 = \frac{E_0}{2(1+v_0)} \quad (6)$$

is the shear modulies of the bond material, and $E_0$ and $v_0$ are the elastic constants of this material. Then one could obtain, $$k = \sqrt{\frac{\lambda}{\kappa}} \quad (7)$$

which is the parameter of the interfacial shearing stress.

The interfacial shearing stress was calculated from the measured shearing force on the basis of the formula $$\tau(x) = \tau_{max} e^{-kx} \quad (8)$$

where $$\tau_{max} = kT \quad (9)$$

is the maximum shearing stress, T is the measured force, and k is the factor of the interfacial shearing stress obtained from the formulas above, and it should be calculated according to each particular samples assemblies. The origin of the coordinate x is at the assembly end at which the external force was applied. The calculated shear off stress was 300 psi for the case of a five kg force-at-failure. Note that, actually, only half of the sample was in contact with the copper foil.

Figure 12A:
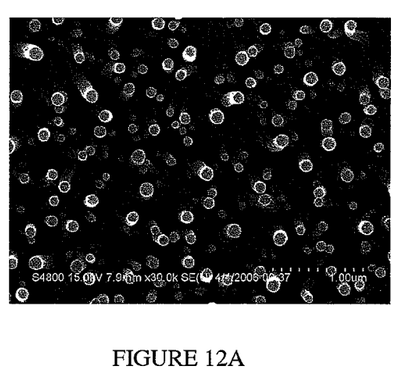
FIG. 12A is a SEM image showing the top view of the CNTs array before the shear off test.
Figure 12B:
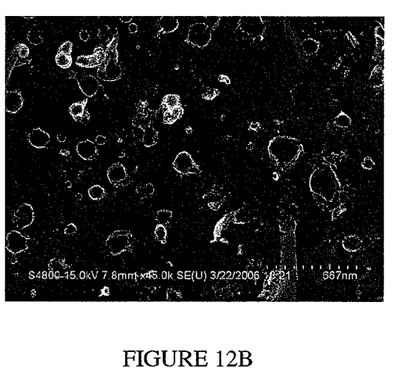
FIG. 12B is a SEM image showing the top view of the CNTs array after the shear off test where most of the CNTs are sheared off from the substrate.

SEM images were taken for the tested samples. FIG. 12A shows the top view for the CNT samples prior to the shear off test. The density of the CNTA was about $10^9/cm^2$, the average diameter of the CNTs was about 80~100 nm, the lengths of the particular CNTs in the CNTA had a variation about 3 μm. This results in a small percentage of CNTs that are not in contact the copper foil.

Figure 12C:
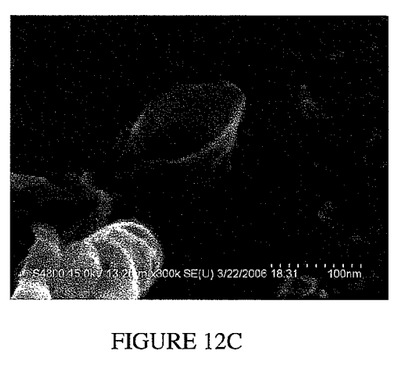
FIG. 12C is a tilt view of the CNT left on the original substrate that reveals that the CNTs have the real hollow center and graphitic outside walls.
Figure 12D:
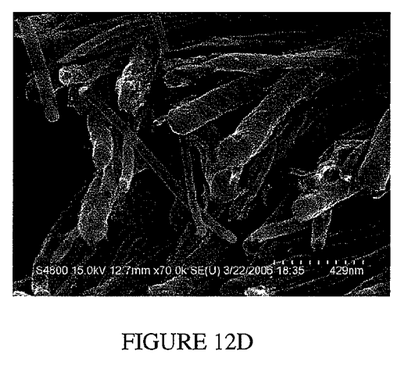
FIG. 12D is a view of the CNTs sheared off from the substrate and that remain on the copper tape.

After the shears off test were conducted, part of the CNTs were sheared off completely from the substrate. With a close look at the substrate, one could observe a ring-shaped bottom part of the remaining CNTs. Only a few very short CNTs, which did not have contact with the copper foil, still remain on the substrate. The tilt view at the CNT roots of the CNTs remained on the substrate: One could see that the roots of the CNTs have graphitic walls with hollow cores at the center.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. A method for increasing thermal conductivity and thermal performance of material comprising an array of any of (i) carbon nanotubes (CNTs) arranged vertically, (ii) carbon nanofibers (CNFs) arranged vertically, and (iii) nanowires arranged vertically, comprising:
repeatedly applying a compressive force to said material, wherein the compressive force is applied in a direction parallel to the any of (i) carbon nanotubes (CNTs) arranged vertically, (ii) carbon nanofibers (CNFs) arranged vertically, and (iii) nanowires arranged vertically.

2. The method of claim 1, wherein said compressive force is applied to said material at least four times.

3. The method of claim 1, wherein said compressive force repetitively applied to said material until a resulting increase in thermal conductivity of said material is less than a predefined threshold.

4. The method of claim 1, said array comprising individually separated, rod-like or tube-like nano-structures.

5. The method of claim 4, wherein said individually separated, rod-like or tube-like nano-structures having a coverage density of between 15 and 40 percent.

6. The method of claim 4, said individually separated, rod-like or tube-like nano-structures having a coverage density of between 25 and 40 percent.

7. A micro-cooler manufactured in accordance with the method of claim 1.

8. A method of rapid thermal annealing (RTA) of a material of an array comprised of any of carbon nanotubes (CNTs), carbon nanofibers (CNFs), or nanowires, comprising:

placing said array at room temperature in an oxygen free environment;

annealing said array at a temperature higher than a growth temperature of said array; and soaking said array in an oxygen free environment at said annealing temperature;

said RTA improving any of quality of said array material, reduction of interfacial thermal resistance, and bonding strength of said array material to a substrate.

9. The method of claim 8, said step of placing said array in a chamber at room temperature in an oxygen free environment, further comprising:

pumping nitrogen gas and argon gas into said environment.

10. The method of claim 9, further comprising:

placing said array in said environment for a period of about five minutes.

11. The method of claim 8, said annealing including reaching a desired annealing temperature within thirty seconds.

12. The method of claim 11, wherein said annealing temperature is within a range of 800 to 1050 degrees Celsius.

13. The method of claim 8, said soaking said array in an oxygen free environment at said annealing temperature further comprising:

pumping gas nitrogen and argon gas into said environment.

14. The method of claim 13, further comprising: placing said array in said environment for a period of one minute.

15. The method of claim 8, said array comprising individually separated, rod-like or tube-like nano-structures.

16. The method of claim 15, said individually separated, rod-like or tube-like nano-structures having a coverage density of between 15 and 40 percent.

17. The method of claim 15, said individually separated, rod-like or tube-like nano-structures having a coverage density of between 25 and 40 percent.

18. A micro-cooler manufactured in accordance with the method of claim 8.

* * * * *